United States Patent [19]

Cragoe, Jr. et al.

[11] 3,931,239

[45] Jan. 6, 1976

[54] 6-OXO-7-SUBSTITUTED-6H-INDENO-[5,4-B]FURAN(AND THIOPHENE)-CARBOXYLIC ACIDS

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[22] Filed: Apr. 3, 1974

[21] Appl. No.: 457,662

[52] U.S. Cl. .................. 260/346.2 M; 260/240 R; 260/247.2 A; 260/330.5; 260/293.58; 424/275; 424/285
[51] Int. Cl.² ........................................ C07D 307/77
[58] Field of Search ...... 260/346.2 M, 240 R, 330.5

[56] References Cited
UNITED STATES PATENTS
3,483,226  12/1969  Baran .................. 260/346.2 M Primary Examiner—Henry R. Jiles
Assistant Examiner—Bernard I. Dentz
Attorney, Agent, or Firm—Michael C. Sudol, Jr.; J. Jerome Behan; James A. Arno

[57] ABSTRACT

6-Oxo-7-substituted -6H-indeno-[5,4-b]furan(and thiophene)carboxylic acids; the 1,2,7,8-tetrahydro; 7,8-dihydro; and 1,2-dihydro derivatives; and the salt, ester and amide derivatives thereof are disclosed having diuretic-saluretic and antihypertensive activity.

20 Claims, No Drawings

6-OXO-7-SUBSTITUTED-6H-INDENO-[5,4-B]FURAN(AND THIOPHENE)-CARBOXYLIC ACIDS

BACKGROUND OF THE INVENTION

This invention relates to certain indenofurans and indenothiophenes having diuretic-saluretic and antihypertensive pharmacological activity. Further, this invention relates to processes for the preparation of such compounds; pharmacological compositions comprising such compounds; and to methods of treatment comprising administering such compounds and compositions for the alleviation of symptoms associated with electrolyte imbalance and fluid retention such as hypertension and edema.

The compounds of this invention may be represented by the following generic structure:

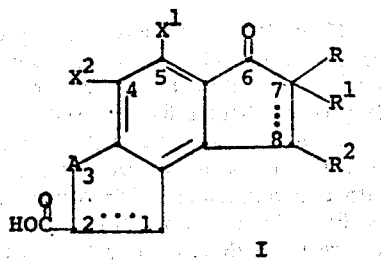

I wherein the dotted lines indicate 1,2-, 7,8-, and 1,2,7,8-unsaturated embodiments; A is oxygen or sulfur; R is hydrogen, lower alkyl or halo; $R^1$ is lower alkyl, cycloalkyl, or aralkyl; or R and $R^1$, together with the carbon atom to which they are attached, may be joined to form a cycloalkyl radical having from 3 to about 6 carbon atoms; $R^2$ is hydrogen, lower alkyl, or phenyl; $X^1$ is lower alkyl or halo; $X^2$ is hydrogen, lower alkyl or halo. A 7-alkylidene embodiment is characterized in that the substituent at the 7-position is $=CR^3R^4$; wherein $R^3$ and $R^4$ are independently selected from the group consisting of hydrogen, lower alkyl, cycloalkyl, aryl, and aralkyl.

Also within the scope of the present invention are the respective salt, ester and amide derivatives of the above-described compounds.

For convenience, these compounds will collectively be referred to hereinafter as "indenofurans".

Pharmacological studies show that the indenofurans of the present invention are effective diuretic and saluretic agents which can be used in the treatment of conditions associated with electrolyte and fluid retention such as edema and hypertension. Thus, when administered in therapeutic dosages in conventional vehicles, the compounds of this invention effectively reduce the amount of sodium and chloride ions in the body, lower dangerous excesses of fluid levels to acceptable levels and in general alleviate conditions associated with edema and hypertension.

Thus it is an object of the present invention to provide the indenofurans of the above general description and to provide processes for preparation of such compounds. Further objects of this invention are to provide pharmaceutical compositions comprising such indenofurans and to provide methods of treatment comprising administering such compounds and compositions.

DETAILED DESCRIPTION OF THE INVENTION

For purposes of description, the indenofurans of the present invention (structure I above) may be represented in a 5-member subgeneric classification according to the following structural formulae:

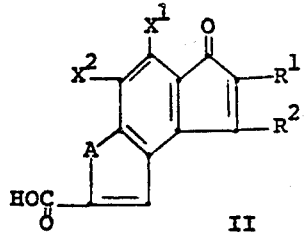

II

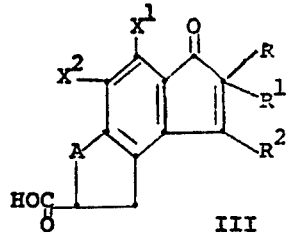

III

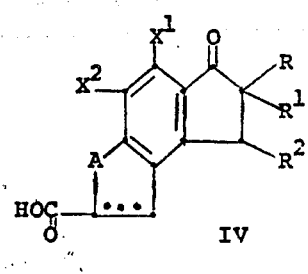

IV

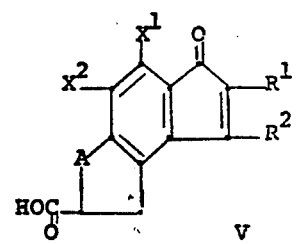

V

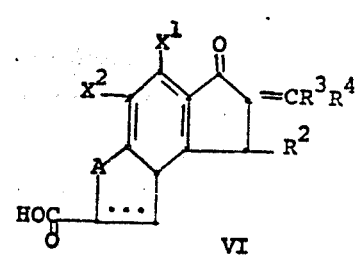

VI wherein A, $X^2$, $X^1$, R, $R^1$, $R^2$, $R^3$, and $R^4$ have previously been defined. The dotted line in structures IV and VI indicates provision for both the 1,2-dihydro and unsaturated forms.

The preferred indenofurans of the present invention are those wherein A is oxygen; R is hydrogen, lower alkyl having from 1 to about 6 carbon atoms, or halogen such as chloro, bromo and fluoro; $R^1$ is lower alkyl having from 1 to about 6 carbon atoms, cycloalkyl having from 3 to about 6 carbon atoms, or aralkyl having from 7 to about 20 carbon atoms; R and $R^1$ are joined together with the carbon to which they are attached to form a cycloalkyl radical having from 3 to about 6 carbon atoms; $R^2$ is hydrogen, lower alkyl having from 1 to about 6 carbon atoms, or phenyl; $R^3$ and $R^4$ are independently selected from hydrogen, lower alkyl having from 1 to about 6 carbons atoms, cycloalkyl having from 3 to about 6 carbon atoms, phenyl, or aralkyl having from 7 to about 20 carbon atoms; $X^1$ is lower alkyl having from 1 to about 6 carbon atoms, or halogen such as chloro, fluoro and bromo; $X^2$ is hydrogen, lower alkyl having from 1 to about 6 carbon atoms, or halogen such as chloro, fluoro and bromo.

Of the non-toxic pharmaceutically acceptable salt, ester and amide derivatives of I, the preferred salts are those of the alkali metals-principally sodium and potassium; the preferred esters are those derived from lower alkanols having from 1 to about 6 carbon atoms; the preferred amides are those derived from mono- and di-lower alkyl amines and hetero amines such as piperidine, morpholine and the like.

The indenofurans of the present invention may be prepared essentially by two basic schemes of synthesis, A and B.

Central to scheme A is an appropriately substituted 5-hydroxyindanone or derivative having the structure:

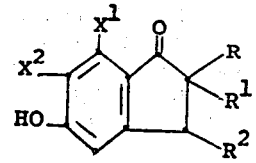

Ia wherein $X^1$, $X^2$, R, $R^1$ and $R^2$ have been previously defined. Representative indanones of structure Ia and their 5-alkoxy or alkyl thio derivatives wherein R is halo or hydrogen have been fully disclosed in U.S. Pat. Nos. 3,668,241 (June 6, 1972) and 3,704,314 (Nov. 28, 1972) which patents are incorporated herein by reference. Other such indanones (R = lower alkyl) are prepared by Friedel-Crafts alkylation of the parent structure or derivatives thereof (Step B, infra).

Scheme A may generally be depicted in the following manner:

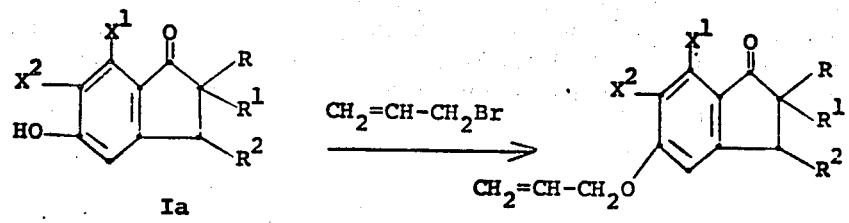

Ia

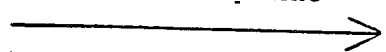
Claisen Rearrangement

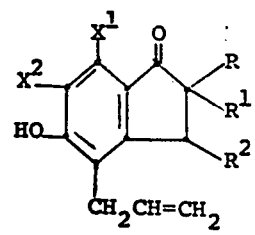

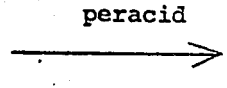
peracid

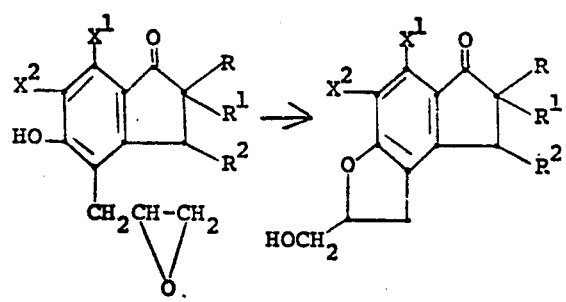

oxidation 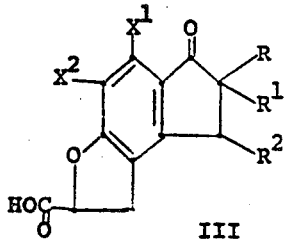
$\longrightarrow$

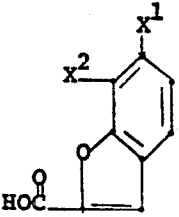  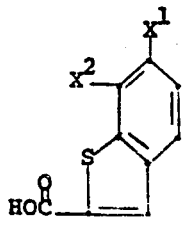

Ib            Ic

According to Scheme A, an appropriately substituted indanone Ia, is reacted with allyl bromide to yield the corresponding 5-allyl ether. Typically the allyl bromide is employed in excess; in fact it may serve as the reaction solvent. Other solvents, provided they are compatible with the desired course of reaction may be employed, for example, ethanol, dimethylformamide and the like. Typically the reaction is conducted in the presence of a base such as sodium alkoxide, potassium carbonate and the like at a temperature in the range of from about 25° to about 100°C. and is substantially complete in from about 0.5 to about 2 hours. The Claisen rearrangement to obtained the 4-allyl species is effected by continued heating at from about 100° to about 220°C. Alternately the 5-allyloxy species may be separated; dissolved in a solvent such as N,N-dimethylaniline, N,N-diethylaniline and the like; and heated at the reflux temperature of the solvent for 0.5 to 4 hours to yield the 4-allyl species. The basic indenofuran nucleus is obtained from the 4-allyl species by treating the latter with a peracid such as m-chloroperbenzoic, peracetic acid and the like in a solvent such as methylene chloride, chloroform, acetic acid and the like at a temperature of from about 0° to the reflux temperature of the solvent. Oxidation of the resulting hydroxymethyl substituted indenofuran yields the indenofurans of the present invention. Typically the oxidation is effected by oxidizing agents such as chromic acid, m-chloroperbenzoic acid, potassium permanganate and the like in a solvent such as water, dilute sulfuric acid, acetone and the like; the temperature of reaction is typically in the range of from about 0° to the reflux temperature of the solvent.

Scheme A is most suitable for the preparation of the saturated species of the present invention represented by structure III, above-depicted. However, the 1,2-dihydro-7,8-unsaturated and the 1,2-dihydro-7-alkylidene embodiments (above-given structures V and VI, respectively) are readily obtained from III by halogenation and dehydrohalogenation.

Scheme B is particularly suited for the preparation of the 1,2-unsaturated embodiments, II, IV, and VI (above); the 1,2-dihydro and 1,2,7,8-tetrahydro embodiments are readily obtainable therefrom by reduction. Central to scheme B is an appropriately 6,7-disubstituted benzofuran (or benzothiophene)-2-carboxylic acid (Ib and Ic, respectively, below):

wherein $X^2$ and $X^1$ have previously been defined. Such benzofuran and benzothiophene compounds are known and available. See for example U.S. Pat. Nos. 3,627,785 (Dec. 14, 1971) and 3,651,094 (Mar. 21, 1972), which patents are incorporated herein by reference. Alternately such compounds may readily be prepared by known procedures. For example, the benzofuran of structure Ib may readily be prepared from an appropriately 2,3-disubstituted phenol in reaction with malic acid in concentrated sulphuric acid to provide the corresponding disubstituted coumarin which upon bromination and subsequent treatment with potassium hydroxide in ethanol yields Ib.

According to scheme B, an appropriate benzofuran (or benzothiophene)-2-carboxylic acid (above) is reacted under Friedel-Crafts conditions with a carboxylic acid halide (or anhydride) of the formula:

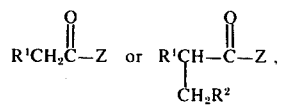

wherein $R^1$ and $R^2$ have previously been defined and Z is halogen such as chloro or bromo, to yield the corresponding 5-acyl species:

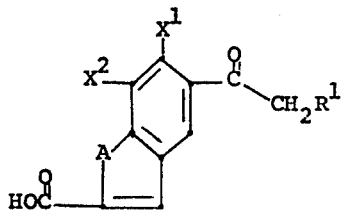   and   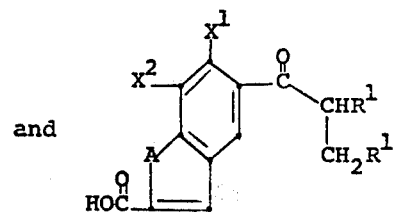

VIIa                VIIb respectively, wherein A is oxygen or sulphur. Suitable catalysts for the reaction are aluminum chloride, tin (IV) chloride, concentrated sulphuric acid and the like. The reaction solvent and temperature are not critical inasmuch as any solvent which is inert to the acyl halide/benzofuran (benzothiophene) reactants may be employed. In this regard, suitable solvents include aliphatic and cycloaliphatic hydrocarbons such as heptane, cyclohexane, and the like; nitrohydrocarbons such as nitrobenzene and the like; and halogenated hydrocarbons such as carbon tetrachloride, methylene chloride, and the like. Typically the reaction is conducted at from 0° to the reflux temperature of the particular solvent employed.

The Friedel-Crafts product is prepared for cyclialkylation to the ultimate indenofuran of this invention by either of two methods. In the case of structure VIIa, a 2'-methylene derivative is prepared via a Mannich intermediate by treating VIIa is paraformaldehyde in the presence of a secondary amine, such as dimethylamine hydrochloride, and the like:

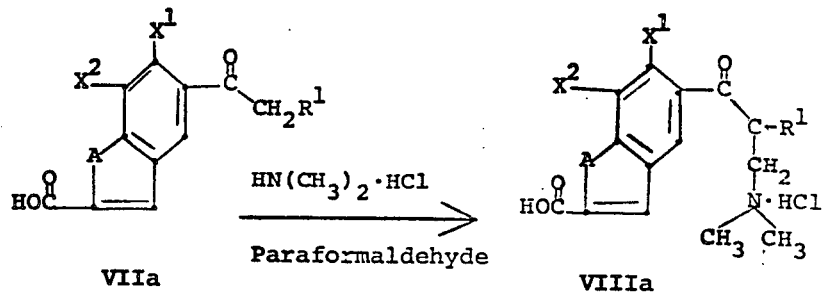

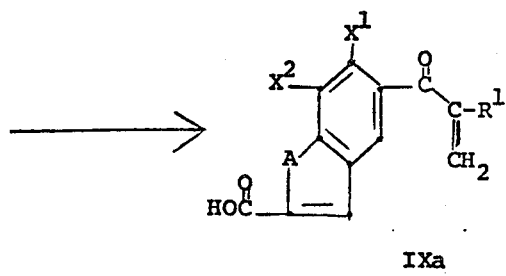

The 2'-methylene species (IXa) is obtained from the Mannich intermediate (VIIIa) on treatment with aqueous sodium bicarbonate, sodium acetate or anhydrous dimethylformamide. In the case of structure VIIb, a suitable 2'-methylene derivative is prepared by halogenating and then dehydrohalogenating according to the following process:

Cyclialkylation of IXa and IXb, thus prepared, yields the indenofurans of the present invention. The cyclialkylation is effected by treatment with a Lewis Acid such as concentrated sulphuric, polyphosphoric acid, boron trifluoride and the like at a temperature of from about 0° to about 6°C. The following equations illustrate this process:

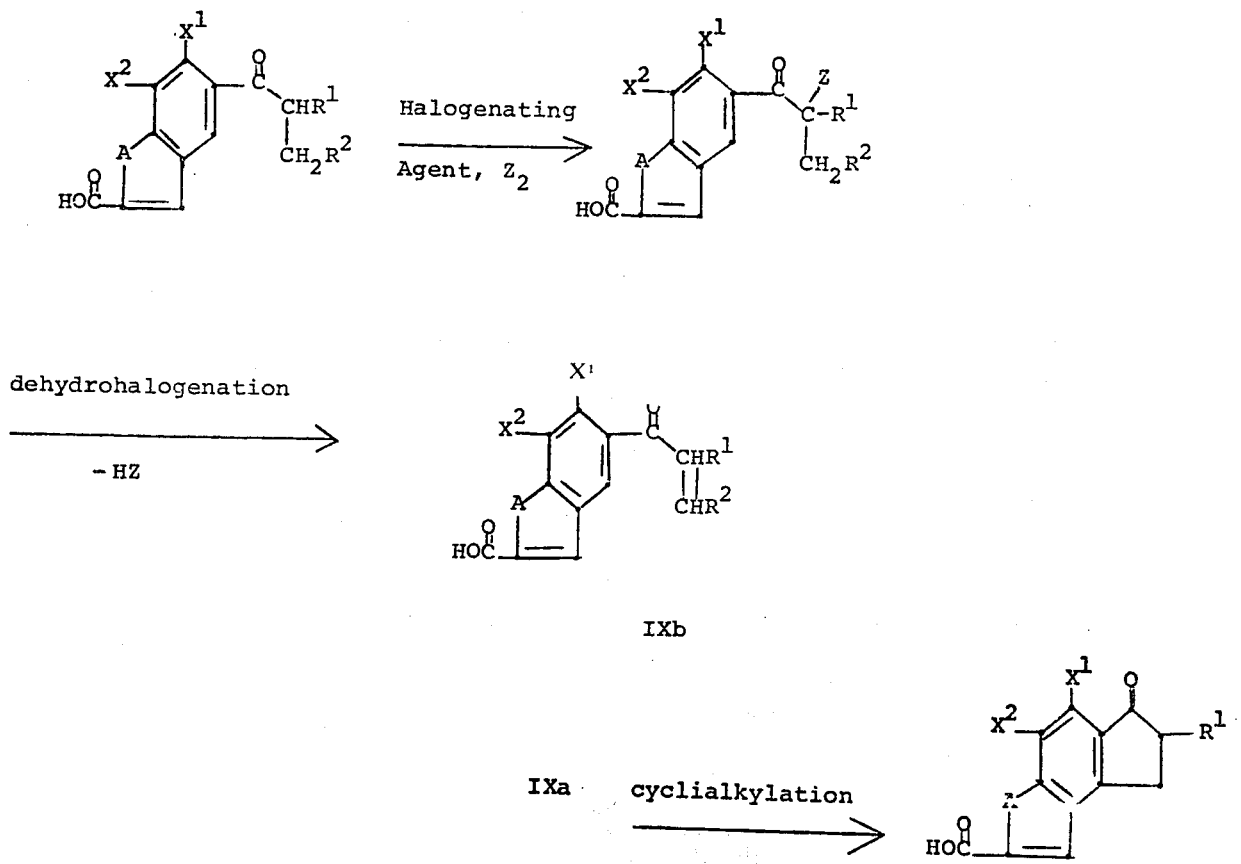

IXb cyclialkylation
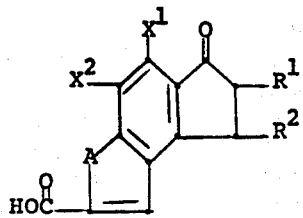

All embodiments of the present invention may be obtained from the above-described 1,2-unsaturated embodiments. For example, 7,8-unsaturated and 7-alkylidene embodiments are readily prepared by halogenation and dehydrohalogenation as previously described under Scheme A; 1,2-dihydro embodiments are readily prepared by reduction with sodium amalgam followed by oxidation of the resulting carbinol (which are also diuretic/saluretic and antihypertensives) to the desired keto form. The following equation generally illustrates this process.

Wherein A, $R^1$, $R^2$, R, $X^2$, and $X^1$ have been defined and Z is halogen such as bromo, chloro, iodo and the like. The above-depicted alkylation is effected by first heating the 7-substituted indenofuran with a suitable base, for example, an alkali metal hydride such as sodium hydride and the like, or an alkali metal alkoxide, for example potassium tertiary butoxide and the like, other bases which may be employed include sodium amide, lithium amide and the like. The resulting carbanion is then treated with an alkylating agent RZ. Any solvent which is inert or substantially inert to the reac-

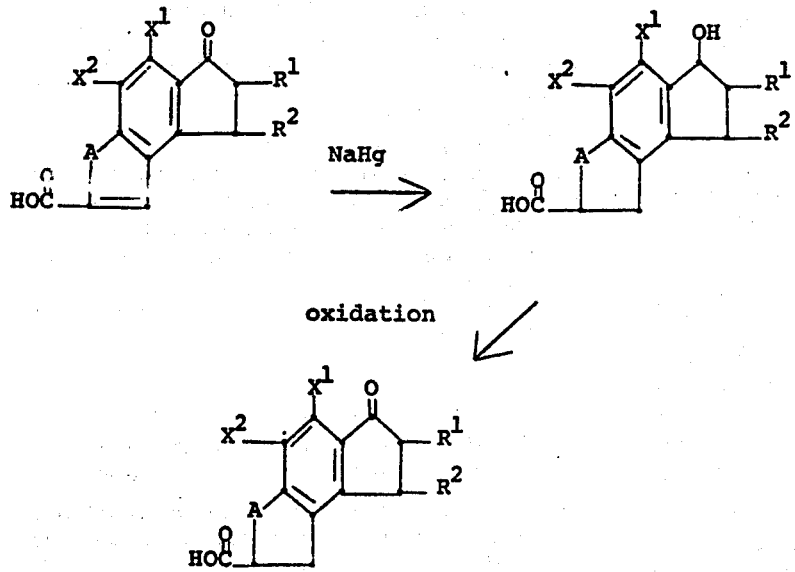

Typically the reduction is carried out in excess aqueous sodium bicarbonate solution, and typically the reaction is complete in from 2 to about 24 hours at 0° to about 25°C. Suitable oxidizing agent include chromic acid, potassium permangante, and the like. Typically the oxidation is conducted in a solvent such as acetone, water and the like.

Finally the 7,7-disubstituted embodiments are conveniently prepared by alkylation according to the following generalized equation:

tants employed may be used. Suitable solvents include 1,2-dimethoxy ethane, tertiary butanol, benzene, dimethylformamide and the like. The reaction may be conducted at a temperature in the range of from about 25° to about 100°C.

As previously mentioned, included within the scope of this invention are the ester and amide derivatives of the instant products which are prepared by conventional methods well known to those skilled in the art. Thus, for example, the ester derivative may be pre-

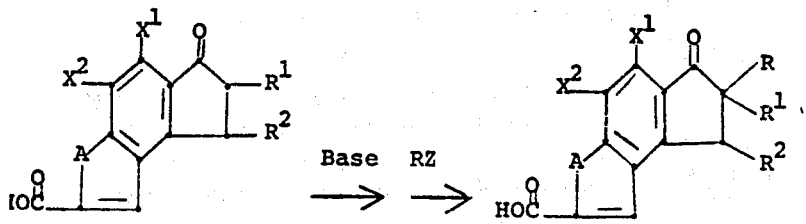

pared by the reaction of an indenofuran- or indenothiophene-2-carboxylic acid of this invention with an alcohol, for example, with a lower alkanol. The amide derivatives may be prepared by converting the same acid to its corresponding acid chloride by treatment with thionyl chloride followed by treating said acid chloride with ammonia, an appropriate mono-lower alkylamine, di-lower alkyl amine or a hetero amine, such as piperidine, morpholine and the like, to produce the corresponding amide compound. These and other equivalent methods for the preparation of the ester and amide derivatives of the instant products will be apparent to one having ordinary skill in the art and to the extent that said derivatives are both non-toxic and physiologically acceptable to the body system, said derivatives are the functional equivalent of the corresponding free acids of the present invention.

The examples which follow illustrate the indenofuran products of the present invention and the methods by which they are prepared. However, the examples are illustrative only and it will be apparent to those having ordinary skill in the art that all the products embraced by the above-given description of the present invention may also be prepared in an analogous manner by substituting the appropriate starting materials for those set forth in the examples.

EXAMPLE 1

4,5-Dimethyl-6-oxo-7-isopropyl-1,2,7,8-tetrahydro-6H-indeno[5,4-b]furan-2-carboxylic acid Step A: 7,8-Dimethylcoumarin A stirred mixture of 2,3-dimethylphenol (45 g.) and malic acid (50 g.) in concentrated sulfuric acid (100 ml.) is slowly warmed in an oil bath to 130°C. and maintained at that temperature until the evolution of carbon monoxide ceases. The reaction mixture is poured into ice water (1 l.) affording 45 g. of 7,8-dimethylcoumarin which melts at 122°–3°C.

Step B: 6,7-Dimethylbenzofuran-2-carboxylic acid

Bromine (28 g.) in chloroform (20 ml.) is added dropwise to a solution of 7,8-dimethylcoumarin (30 g.) in chloroform (50 ml.); the reaction is stirred for 0.5 hours at 25°C.; the solvent is distilled off at reduced pressure and the residual oil is poured protionwise into an ice chilled slurry of potassium hydroxide (90 g.) in ethanol (300 ml.). The reaction mixture is stirred at 40°C. for 0.5 hours, warmed to 60° then poured into ice water (1.2 l.). The aqueous solution is washed with ether and acidified with hydrochloric acid to afford 28 g. of 6,7-dimethylbenzofuran-2-carboxylic acid which melts at 235°–7°C.

Step C:
2,3-Dihydro-6,7-dimethylbenzofuran-2-carboxylic acid 6,7-Dimethylbenzofuran-2-carboxylic acid (11 g.) is dissolved in 165 ml. of saturated aqueous sodium bicarbonate, diluted with water (60 ml.) and cooled to 5°C. Thereafter sodium amalgam (1%, 610 g.) is added. The mixture is stirred 18 hours at room temperature; the aqueous phase separated and acidified with hydrochloric acid to afford 9 g. of 2,3-dihydro-6,7-dimethyl-benzofuran-2-carboxylic acid which melts at 182°C.

Step D:
2,3-Dihydro-5-isovaleryl-6,7-dimethylbenzofuran-2-carboxylic acid

To a stirred solution of 2,3-dihydro-6,7-dimethylbenzofuran-2-carboxylic acid (9 g.) and isovaleryl chloride (7.5 g.) in dichloromethane (100 ml.) at 5°C. is added aluminum chloride (20 g.) in portions over a 1 hour period. The reaction mixture is stirred at 25° for 18 hours then poured into a mixture of ice (300 g.) and hydrochloric acid (50 ml.) affording 9 lg. of 2,3-dihydro-5-isovaleryl-6,7-dimethyl-benzofuran-2-carboxylic acid which melts at 117° after recrystallization from methylcyclohexane.

Calculated: $C_{16}H_{20}O_4$; C, 69.55; H, 7.30; Found: C, 69.34; H, 7.32.

Step E:
2,3-Dihydro-5-(2-methyleneisovaleryl)-6,7-dimethyl-benzofuran-2-carboxylic acid A mixture 2,3-dihydro-5-isovaleryl-6,7-dimethylbenzofuran-2-carboxylic acid (8.5 g.), paraformaldehyde (2.0 g.), dimethylamine hydrochloride (3.3 g.) and acetic acid (1 ml.) is heated at 95° for 2.5 hours treated with dimethylformamide (75 ml.), heated an additional 3.5 hours then poured into ice water (300 ml.) containing hydrochloric acid (5 ml.). The product is extracted into ether, washed with water, dried over magnesium sulfate and the solvent evaporated at reduced pressure to afford 2,3-dihydro-5-(2-methyleneisovaleryl)-6,7-dimethylbenzofuran-2-carboxylic acid which melts at 97°C. after recrystallization from cyclohexane.

Calculated: $C_{17}H_{20}O_4$; C, 70.81; H, 6.99; Found: C 70.47; H, 7.49.

Step F:
4,5-Dimethyl-6-oxo-7-isopropyl-1,2,7,8-tetrahydro-6H-indeno[5,4-b]furan-2-carboxylic acid A mixture of 2,3-dihydro-5-(2-methyleneisovaleryl)-6,7-dimethylbenzofuran-2-carboxylic acid (5.0 g.) and concentrated sulfuric acid (25.0 ml.) is heated at 57°C. for 6 hours then poured into ice water (300 ml.). The 4,5-dimethyl-6-oxo-7-isopropyl-1,2,7,8-tetrahydro-6H-indeno[5,4-b]furan-2-carboxylic acid which separates is filtered and dried.

EXAMPLE 2

Following the procedure exactly as described in Example 1 except that the 2,3-dimethylphenol of Step A is replaced by an equivalent amount of 2,3-dichlorophenol and 3-ethylphenol, respectively, there is obtained 4,5-dichloro-6-oxo-7-isopropyl-1,2,7,8-tetrahydro-6H-indeno[5,4-b]furan-2carboxylic acid and 5-ethyl-6-oxo-7-isopropyl-1,2,7,8-tetrahydro-6H-indeno[5,4-b]furan-2-carboxylic acid, respectively.

EXAMPLE 3

4,5-Dimethyl-6-oxo-7-isopropyl-7,8-dihydro-6H-indeno-[5,4-b]furan-2-carboxylic acid Step A:
5-Isovaleryl-6,7-dimethylbenzofuran-2-carboxylic acid To a stirred solution of 6,7-dimethylbenzofuran-2- carboxylic acid (9 g.) and isovaleryl chloride (7.5 g.) in dichloromethane (100 ml.) at 5°C. is added aluminum trichloride (20 g.) in portions over a 1 hour period. The reaction mixture is stirred at 25°C. for 18 hours, poured into a mixture of ice (300 g.) and hydrochloric acid (50 ml.) to afford 5-isovaleryl-6,7-dimethylbenzofuran-2-carboxylic acid.

Step B:
5-(2-Methyleneisovaleryl)-6,7-dimethylbenzofuran-2-carboxylic acid

A mixture of 5-isovaleryl-6,7-dimethylbenzofuran-2-carboxylic acid (8.5 g.), paraformaldehyde (2.0 g.), dimethylamine hydrochloride (3.3 g.) and acetic acid (1 ml.) is heated at 95°C. for 2.5 hours, treated with dimethylformamide (75 ml.), heated an additional 3.5 hours, poured into ice water (300 ml.) containing hydrochloric acid (5 ml.). The product is extracted into ether, washed with water, dried over magnesium sulfate, the solvent evaporated at reduced pressure to afford 5-(2-methyleneisovaleryl)-6,7-dimethylbenzofuran-2-carboxylic acid.

Step C:
4,5-Dimethyl-6-oxo-7-isopropyl-7,8-dihydro-6H-indeno[5,4-b]furan-2-carboxylic acid A mixture of 5-(2-methyleneisovaleryl)-6,7-dimethylbenzofuran-2-carboxylic acid (5 g.) and concentrated sulfuric acid (25 ml.) is heated at 57°C. for 6 hours and poured into ice water (300 ml.). The 4,5-dimethyl -6-oxo-7-isopropyl-7,8-dihydro-6H-indeno-[5,4-b]furan-2-carboxylic acid which separates is filtered and dried.

EXAMPLE 4

4,5,7-Trimethyl-6-oxo-7-isopropyl-1,2,7,8-tetrahydro-6H-indeno[5,4-b]furan-2-carboxylic acid A solution of 4,5-dimethyl-6-oxo-7-isopropyl1,2,7,8-tetrahydro-6H-indeno[5,4-b]furan-2-carboxylic acid (0.01 mole) in dimethylformamide (50 ml.) at 15°C. is treated with sodium hydride (50% dispersion in mineral oil, (0.–25 mole). The solution is warmed to 50°C., cooled to 25°C., treated with methyl iodide (0.025 mole) then warmed to 50°C. Thereafter, water (50 ml.) and 10 N sodium hydroxide (2 ml.) are added; the reaction is heated at 95°C. for 0.5 hours then poured into cold 1.0N hydrochloric acid to afford 4,5,7-trimethyl-6-oxo-7-isopropyl-1,2,7,8-tetrahydro-6H-indeno[5,4-b]furan-2-carboxylic acid.

EXAMPLE 5

4,5-Dimethyl-6-oxo-7-isopropyl-6H-indeno[5,4-b]furan-2-carboxylic acid

Step A:
4,5-Dimethyl-6-oxo-7,8-dihydro-7-bromo-7-isopropyl-6H-indeno[5,4-9 furan-2-carboxylic acid A solution of 4,5-dimethyl-6-oxo-7,8-dihydro-7-iso-propyl-6H-indeno[5,4-b]furan-2-carboxylic acid (0.01 mole) in acetic acid (60 ml.) is treated with 48% hydrobromic acid (1 drop) then with bromine (0.01 mole) in acetic acid (10 ml.) during a ten minute period. The solution is poured into ice water (300 ml.) containing sodium bisulfite (1 g.) to afford 4,5-dimethyl-6-oxo-7,8-dihydro-7-bromo-7-isopropyl-6-H-indeno[5,4-b]furan-2-carboxylic acid.

Step B:
4,5-Dimethyl-6-oxo-7-isopropyl-6H-indeno[5,4-b]furan-2-carboxylic acid

A solution of 4,5-dimethyl-6-oxo-7,8-dihydro-7-bromo-7-isopropyl-6H-indeno[5,4-b]furan-2-carboxylic acid (0.01 mole) in dimethylsulfoxide (50 ml.) is treated with 1,5-diazabicyclo[4.3.0]-5-nonene (0.20 mole) and stirred in an inert (nitrogen) atmosphere at 25°C. for 1 hour; poured into 1.0 N hydrochloric acid to afford 4,5-dimethyl-6-oxo-7-isopropyl-6H-indeno-[5,4-b]furan-2-carboxylic acid.

EXAMPLE 6

4,5-Dimethyl-6-oxo-7,8-dihydro-7-isopropylidene-6H-indeno[5,4-b]furan-2-carboxylic acid A solution of 4,5-dimethyl-6-oxo-7,8-dihydro-7-bromo-7-isopropyl-6H-indeno[5,4-b]furan-2-carboxylic acid (0.01 mole) and lithium bromide (0.02 mole) in dimethylformamide (100 ml.) is heated in an inert atmosphere (nitrogen) at 95°C. for 2.0 hours; poured into ice water (300 ml.) to afford 4,5-dimethyl-6-oxo-7,8-dihydro-7-isopropylidene-6H-indeno[5,4-b]furan-2-carboxylic acid.

EXAMPLE 7

4',5'-Dichloro-6'-oxo-1',2',7',8'-tetrahydrospiro(cyclopentane-1,7'-6'H-indeno[5,4-b]furan)-2'-carboxylic acid Step A: 2,3-Dichloro-4-(6-bromohexanoyl)anisole A stirred mixture of 2,3-dichloroanisole (89 g., 0.50 mole) and 6-bromohexanoyl chloride (120 g., 0.59 mole) in methylene chloride (500 ml.) is cooled to 5°C. and treated with aluminum chloride (74 g., 0.56 mole) in portions during a one-half hour period. The reaction mixture is kept at 25°C. for 18 hours, then poured into ice water (1 l.) made acidic with hydrochloric acid. The organic phase is separated washed with water, 2% sodium hydroxide and 1.0 M hydrochloric acid. The methylene chloride is evaporated at reduced pressure. The resulting oil is dissolved in ether, dried over magnesium sulfate, evaporated to 200 ml. and treated with hexane (600 ml.) to afford 2,3-dichloro-4-(6-bromohexanoyl) anisole which melts at 52°–53°C.

Elemental analysis for $C_{13}H_{15}BrCl_2O_2$: Calc.: C, 44.10; H, 4.27; Found: C, 44.33; H, 4.66.

Step B:
2-(4-Chlorobutyl)-5-methoxy-6,7-dichloro-1-indanone

A stirred mixture of 2,3-dichloro-4-(6-bromohexanoyl)anisole (10 g.), dimethylamine hydrochloride (4 g.), paraformaldehyde (2 g.) and acetic acid (0.5 ml.) is heated on a steam bath for two hours, treated with dimethylformamide (30 ml.) and heated an additional 2 ½ hours. The reaction mixture is poured into water, extracted with ether, washed with water and dried over magnesium sulfate. Evaporation of the ether affords 9 g. of crude 2,3-dichloro-4-(6-chloro-2-methylenehexanoyl)-anisole which is cyclialkylated by treatment with concentrated sulfuric acid (50 ml.). The sulfuric acid solution is poured into water (300 ml.) affording 5.8 g. of 2-(4-chlorobutyl)-5-methoxy-6,7-dichloro-1- indanone which melts at 92°C. after recrystallization from cyclohexane.

Elemental analysis for $C_{14}H_{15}Cl_3O_2$: Calc.: C, 52.28; H, 4.70; Cl, 33.07; Found: C, 52.25; H, 4.50; Cl, 33.03.

Step C:
5'-Methoxy-6',7'-dichlorospiro(cyclopentane-1,2'-indanone)

A stirred suspension of sodium hydride (370 mg., 0.0155 mole) in 1,2-dimethoxyethane (250 ml.) is refluxed in an inert atomosphere. A solution of 2-(4-chlorobutyl)-5-methoxy-6,7-dichloro-1-indanone. (4.5 g., 0.014 mole) in 1,2-dimethoxyethane (50 ml.) is added over a 20-minute period and refluxing is maintained for three hours. The solvent is distilled to a volume of 50 ml. and poured into water (300 ml.) affording 2.6 g. of 5'-methoxy-6',7'-dichlorospiro-(cyclopentane-1,2'-indanone) which melts at 170°C. after recrystallization from ethanol-water.

Elemental analysis for $C_{14}H_{14}Cl_2O_2$: Calc: C, 58.97; H, 4.95; Found: C, 58.94; H. 5.00.

Step D:
5'-Hydroxy-6',7'-dichlorospiro-(cyclopentane-1,2'-indanone)

A stirred mixture of 5'-methoxy-6',7'-dichlorospiro-(cyclopentan-1,2'-indanone) (2.6 g., 0.0091 mole) and pyridine hydrochloride (26 g.) is heated at 185°C. for one hour, then poured into water (200 ml.). The 5'-hydroxy-6',7'-dichlorospiro-(cyclopentane-1,2'-indanone) which separates (2.3 g.) melts at 236°C. after recrystallization from nitromethane.

Elemental analysis for $C_{13}H_{12}Cl_2O_2$: Calc.: C, 57.55; H, 4.46; Found: C, 57.77; H, 4.54.

Step E:
5'Allyloxy-6',7'-dichlorospiro-(cyclopentane-1,2'-indanone)

A stirred mixture of 5'-hydroxy-6',7'-dichlorospiro (cyclopentane-1,2'-indanone) (8.13 g., 0.03 mole) potassium carbonate (4.55 g.) and allyl bromide (2.85 ml.) in dimethylformamide (50 ml.) is heated at 55°C. in an inert atmosphere for 1 hour then poured into water (300 ml.) affording 5'-allyloxy-6',7'-dichlorospiro-(cyclopentane-1,2'-indanone (9.0 g.) which melts at 110°-2°C. after recrystallization from cyclohexane.

Elemental analysis for $C_{16}H_{16}Cl_2O_2$: Calc.: C, 61.75; H, 5.18; Found: C, 61.45; H, 5.18.

Step F: 4'-Allyl-5'-hydroxy-6',7'-dichlorospiro (cyclopentane-1,2'-indanone)

A mixture of 5'-allyloxy-6',7'-dichlorospiro (cyclopentane-1,2'-indanone) (3.0 g., 0.0096 mole) and N,N-diethylaniline (30 ml.) is refluxed for 1 ½ hours then poured into water (300 ml.) containing hydrochloric acid (50 ml.). The product is extracted into ether (100 ml.) washed with 1N hydrochloric acid, water, dried over magnesium sulfate and the ether evaporated affording 4'-allyl-5'-hydroxy-6',7'-dichlorospiro(cyclopentane-1,2'-indanone) (1.7 g.) which melts at 103°C. after recrystallization from butyl chloride-hexane.

Elemental analysis for $C_{16}H_{16}Cl_2O_2$: Calc.: C, 61.75; H, 5.18: Found: C, 61.91; H, 5.34.

Step G:
4',5'-Dichloro-2'-hydroxymethyl-1',2'7',8'-tetrahydrospiro (cyclopentane-1,7'-6'H-indeno[5,4-b]furan-6'-one)

A solution of 4'-allyl-5'-hydroxy-6',7'-dichlorospiro(cyclopentane-1,2'-indanone) (9.3 g., 0.03 mole) and m-chloroperbenzoic acid (6.5 g.) in methylene chloride (125 ml.) is refluxed for 18 hours, cooled, washed with dilute aqueous sodium bicarbonate, saturated sodium chloride solution, and dried over magnesium sulfate. Evaporation of the methylene chloride affords 4',5'-dichloro-2'-hydroxymethyl-1',2',7',8'-tetrahydrospiro (cyclopentane-1,7',6'H-indeno[5,4-b]furan-6'-one) which melts at 123°-5°C. after recrystallization from ether.

Elemental analysis for $C_{16}H_{16}Cl_2O3$: Calc.: C, 58.73; H, 4.93; Cl, 21.67; Found: C, 58.44; H, 4.83; Cl, 21.72.

Step H:
4',5'-Dichloro-6'-oxo-1',2',7',8'-tetrahydrospiro(cyclopentane-1,7'-6'-H-indeno[5,4-b]furan)-2'-carboxylic acid A stirred solution of 4',5'-dichloro-2'-hydroxymethyl-1',2',7',8'-tetrahydrospiro(cyclopentane-1,7'-6'H-indeno[5,4-b]furan-6'-one) (0.58 g., 1.77 m moles) in acetone (25 ml.) is treated with an oxidizing solution comprised of chromium trioxide (0.35 g.), water (2.5 ml.) and sulfuric acid (0.31 ml.). The reaction is stirred at 25°C. for 18 hours, then the acetone phase is decanted and evaporated at reduced pressure. The residue is dissolved in ether, washed with dilute hydrochloric acid, extracted into sodium bicarbonate, acidified, extracted into ether, washed with water and dried over magnesium sulfate. Evaporation of the ether affords 4',5'-dichloro-6'-oxo-1',2',7',8'-tetrahydrospiro(cyclopentane-1,7'-6'H-indeno-[5,4-b]furan)-2'-carboxylic acid which melts at 195°C. after recrystallization from toluene.

Elemental analysis for $C_{16}H_{14}Cl_2O_4$: Calc.: C, 56.32; H, 4.14; Found: C, 56.25; H, 4.28.

EXAMPLE 8

4,5-Dimethyl-6-oxo-7-propyl-7,8-dihydro-6H-indeno[5,4-b]-furan-2-carboxylic acid Step A:
4,5-Dimethyl-6-valerylbenzofuran-2-carboxylic acid A stirred suspension of 4,5-dimethylbenzofuran-2-carboxylic acid (18 g.) and valeryl chloride (15 g.) in methylene chloride (300 ml.) is cooled to 5°C. and treated with aluminum chloride (40 g.) in portions during a ½ hour period during which time the suspended reactant dissolves. The reaction mixture is stirred at 25° for 2 days then poured into ice water (500 ml.) containing hydrochloric acid (50 ml.). The product (21 g.) separates from the biphasic solution, is filtered and recrystallized from ethanol-water affording 4,5-dimethyl-6-valerylbenzofuran-2-carboxylic acid which melts at 188°-9°C.

Elemental analysis for $C_{16}H_{18}O_4$: Calc.: C, 70.05; H, 6.61; Found: C, 69.94; H, 6.79.

Step B: 4,5-Dimethyl-6-(2-methylenevaleryl) benzofuran-2-carboxylic acid

A mixture of 4,5-dimethyl-6-valerylbenzofuran-2-carboxylic acid (15 g.) paraformaldehyde (3.5 g.) and dimethylamine hydrochloride (7 g.) in p-dioxane (100 ml.) is refluxed for 8 hours and cooled. The 4,5-dimethyl-6-[(2-dimethylaminomethyl)valeryl]benzofuran-2-carboxylic acid hydrochloride which separates is filtered, dried, and dissolved in acetic acid (200 ml.) containing sodium acetate (20 g.). The reaction mixture is refluxed for two hours then poured into water (250 ml.) containing hydrochloric acid (25 ml.) affording 4,5-dimethyl-6-(2-methylenevaleryl)-benzofuran-2-carboxylic acid which melts at 172° after recrystallization from butyl chloride.

Elemental analysis for $C_{17}H_{18}O_4$: Calc: C, 71.31; H, 6.34; Found: C, 71.10; H, 6.54.

Step C: 4,5-Dimethyl-6-oxo-7-propyl-7,8-dihydro-6H-indeno[5,4-b]furan-2-carboxylic acid A solution of 4,5-dimethyl-6-(2-methylenevaleryl)-benzofuran-2-carboxylic acid (6 g.) in concentrated sulfuric acid (80 ml.) is stirred 18 hours at 25°C. then poured into ice water (500 ml.) affording 4,5-dimethyl-6-oxo-7-propyl-7,8-dihydro-6H-indeno[5,4-b]-furan-2-carboxylic acid which melts at 287°C. after recrystallization from acetic acid.

Elemental analysis for $C_{17}H_{18}O_4$: Calc: C, 71.31; H, 6.34; Found: C, 71.58; H, 6.42.

EXAMPLE 8a

Sodium[4,5-dimethyl-6-oxo-7-propyl-7,8-dihydro-6H-indeno[5,4-b]furan-2-carboxylate]

To a saturated ethanolic solution of 4,5-dimethyl-6-oxo-7-propyl-7,8-dihydro-6H-indeno[5,4-b]-furan-2-carboxylic acid is added, dropwise, a saturated ethanolic solution of sodium hydroxide. The resulting salt precipitate is collected by filtration and dried to provide sodium [4,5-dimethyl-6-oxo-7-propyl-7,8-dihydro-6H-indeno[5,4-b]furan-2-carboxylate.]

EXAMPLE 8b

N-Ethyl[4,5-dimethyl-6-oxo-7-propyl-7,8-dihydro-6H-indeno[5,4-b]furan-2-carboxamide]

A solution of 4,5-dimethyl-6-oxo-7-propyl-7,8-dihydro-6H-indeno[5,4-b]furan-2-carboxylic acid (0.6 g.) and thionyl chloride (0.3 ml.) in benzene (10 ml.) is refluxed for one hour. The solvent is distilled at reduced pressure and the residue is treated with benzene (20 ml.) and ethylamine (0.5 ml.). After one hour the reaction mixture is poured into water and extracted with ether which is washed with dilute hydrochloric acid and aqueous sodium bicarbonate. The ether solution is dried over magnesium sulfate and evaporated at reduced pressure to afford N-ethyl[4,5-dimethyl-6-oxo-7-propyl-7,8-dihydro-6H-indeno[5,4-b]furan-2-carboxamide].

EXAMPLE 8c

Ethyl[4,5-dimethyl-6-oxo-7-propyl-7,8-dihydro-6H-indeno-[5,4-b]furan-2-carboxylate]

To a solution of 4,5-dimethyl-6-oxo-7-propyl-7,8-dihydro-6H-indeno[5,4-b]furan-2-carboxylic acid (8.0 g.) in ethanol (50 ml.) is added borontrifluoride etherate (13 ml.). The reaction mixture is refluxed for 0.5 hour, treated with water and cooled to afford ethyl [4,5-dimethyl-6-oxo-7-propyl-7,8-dihydro-6H-indeno[5,4-b]-furan-2-carboxylate] after filtration and drying.

EXAMPLE 9

4,5-Dichloro-7-ethyl-6-oxo-8-phenyl-1,2,7,8-tetrahydro-6H-indeno[5,4-b]furan-2-carboxylic acid

Step A: 2',3'-Dichloro-4'-methoxybutyropheone

A solution of 2',3'-dichloro-4'-hydroxybutyrophenone (57 g., 0.0248 mole) in methanol (400 ml.) is heated to reflux. A solution of sodium hydroxide (40 g.) in water (100 ml.) and dimethyl sulfate are added alternately in small portions over a ½ hour period such that the reaction mixture is always alkaline. On cooling 2',3'-dichloro-4'-methoxybutyropheone separates which melts at 42°–44°C. after recrystallization from hexane.

Elemental analysis for $C_{11}H_{12}Cl_2O_2$: Calc.: C, 53.46; H, 4.89; Found: C, 53.71; H, 4.73.

Step B: 2,3-Dichloro-4-(2-benzylidenebutyryl)anisole

A stirred mixture of benzaldehyde (19.4 g., 0.183 mole) and 2',3'-dichloro-4-methoxybutyropheone (42.2 g., 0.183 mole) in ethanol (350 ml.) is treated with 20% sodium hydroxide (35.9 ml.). The reaction is stirred for 22 hours during which time the 2,3-dichloro-4-(2-benzylidenebutyryl)anisole separates mp= 127°–130°C.

Elemental analysis for $C_{18}H_{16}Cl_2O_2$: Calc.: C, 64.49; H, 4.81; Found: C, 64.39; H, 4.79.

Step C: 2-Ethyl-3-phenyl-5-methoxy-6,7-dichloro-1-indanone

A stirred mixture of 2,3-dichloro-4-(2-benzylidenebutyryl)anisole (55.6 g., 0.166 mole) and polyphosphoric acid (550 g.) is heated at 95°–100°C. for six hours then at 80°–85° for 16 hours, then poured into water (2 l.) affording 2-ethyl-3-phenyl-5-methoxy-6,7-dichloro-1-indanone which melts at 114°–6°C. after recrystallization from acetic acid-water.

Elemental analysis for $C_{18}H_{16}Cl_2O_2$: Calc.: C, 64.49; H, 4.48; Found: C, 64.48; H, 4.87.

Step D: 2-Ethyl-3-phenyl-5-hydroxy-6,7-dichloro-1-indanone

A stirred mixture of 2-ethyl-3-phenyl-5-methoxy-6,7-dichloro-1-indanone (13.9 g., 0.0415 mole) and aluminum chloride (13.6 g., 0.104 mole) in heptane (120 ml.) is refluxed for five hours then cooled. The heptane is decanted and the residue is treated with ice water (100 ml.) containing hydrochloric acid. The gum which separates is extracted into ether, washed with water dried over magnesium sulfate and the ether evaporated at reduced pressure affording 11.3 g. of 2-ethyl-3-phenyl-5-hydroxy-6,7-dichloro-1-indanone which melts at 220°–2°C. after recrystallization from methanol.

Elemental analysis for $C_{17}H_{14}Cl_2O_2$: Calc: C, 63.57; H, 4.39; Found: C, 63.80; H, 4.46.

Step E:
5-Allyloxy-6,7-dichloro-2-ethyl-3-phenyl-1-indanone

5-Allyloxy-6,7-dichloro-2-ethyl-3-phenyl-1-indanone is prepared following substantially the same procedure described in Example 7 Step E using the following substantces:

| | |
|---|---|
| 2-Ethyl-3-phenyl-5-hydroxy-6,7-dichloro-1-indanone | (14 g., 0.044 mole) |
| Potassium Carbonate | (6.6 g., 0.047 mole) |
| Allyl bromide | (5.9 g., 0.049 mole) |
| Dimethylformamide | (75 ml.) |

The above procedure gives 10.4 g. (67%) of 5-allyloxy-6,7-dichloro-2-ethyl-3-phenyl-1-indanone which after recrystallization from ethanol melts at 115°C.

Elemental analysis for $C_{20}H_{18}Cl_2O_2$: Calc.: C, 66.49; H, 5.02; Found: C, 66.78; H, 5.13.

Step F:
4-Allyl-5-hydroxy-6,7-dichloro-2-ethyl-3-phenyl-1-indanone

4-Allyl-5-hydroxy-6,7-dichloro-2-ethyl-3-phenyl-1-indanone is prepared following substantially the same procedure as described in Example 7, Step F using the following substances:

| | |
|---|---|
| 5-Allyloxy-6,7-dichloro-2-ethyl-3-phenyl-1-indanone | (10.7 g., 0.03 mole) |
| N,N-Diethylaniline | (75 ml.) |

The above procedure gives 4.0 g. (37%) of 4-allyl-5-hydroxy-6,7-dichloro-2-ethyl-3-phenyl-1-indanone which after recrystallization from butyl-chloride-hexane melts at 129°C.

Elemental analysis for $C_{20}H_{18}Cl_2O_2$: Calc.: C, 66.49; H, 5.02; Found: C, 65.92; H, 5.31.

Step G:
4,5-Dichloro-1,2,7,8-tetrahydro-2-hydroxymethyl-7-ethyl-6-oxo-8-phenyl-6H-indeno[5,4-b]furan 4,5-Dichloro-1,2,7,8-tetrahydro-2-hydroxymethyl-7-ethyl-6-oxo-8-phenyl-6H-indeno[5,4-b]furan is prepared following substantially the same procedure described in Example 7, Step G using the following substances:

| | |
|---|---|
| 4-Allyl-5-hydroxy-6,7-dichloro-2-ethyl-3-phenyl-1-indanone | (3.9 g., 0.011 mole) |
| Methylene chloride | 40 ml. |
| Sodium acetate | 100 ml. |
| Peracetic acid (40%) | 3 ml. |

The above procedures gives 2.0 g. (50%) of 4,5-dichloro-1,2,7,8-tetrahydro-2-hydroxymethyl-7-ethyl-6-oxo-8-phenyl-6H-indeno[5,4-b]furan which after recrystallization from butyl chloride melts at 169°–70°C.

Elemental analysis for $C_{20}H_{18}Cl_2O_3$: Calc.: C, 63.67; H, 4.81; Found: C, 63.66; H, 4.90.

Step H:
4,5-Dichloro-7-ethyl-6-oxo-8-phenyl-1,2,7,8-tetrahydro-6H-indeno[5,4-b]-furan-2-carboxylic acid 4,5-Dichloro-7-ethyl-6-oxo-8-phenyl-1,2,7,8-tetrahydro-6H-indeno[5,4-b]furan-2-carboxylic acid is prepared following substantially the same procedure described in Example 7, Step H using the following substances:

| | |
|---|---|
| 4,5-Dichloro-1,2,7,8-tetrahydro-2-hydroxymethyl-7-ethyl-6-oxo-8-phenyl-6H-indeno [5,4-b] furan | (1.9 g., 0.005 mole) |
| Acetone | 100 ml. |
| Chromium trioxide | 1.4 g. |
| Sulfuric acid | 1.2 ml. |
| Water | 10 ml. |

The above procedure gives 4,5-dichloro-7-ethyl-6-oxo-8-phenyl-1,2,7,8-tetrahydro-6H-indeno[5,4-b]furan-2-carboxylic acid which after recrystallization from toluene melts at 222°C.

Elemental analysis for $C_{20}H_{16}Cl_2O_4$: Calc.: C, 61.40; H, 4.12; Found: C, 61.24; H, 4.06.

EXAMPLE 10

4,5-Dimethyl-6-oxo-7-propyl-6H-indeno[5,4-b]furan-2-carboxylic acid

Step A: 4,5-Dimethyl-6-oxo-7-bromo-7-propyl 7,8-dihydro-6H-indeno[5,4-b]furan-2-carboxylic acid A stirred solution of 4,5-dimethyl-6-oxo-7-propyl-7,8-dihydro-6H-indeno[5,4-b]furan-2-carboxylic acid (2.86 g., 0.01 mole) in tetrahydrofuran (75 ml.) is treated during a ½ hour period with a solution of pyrrolidone-2-hydrotribromide (4.96 g., 0.01 mole) in tetrahydrofuran. Addition of water (500 ml.) to the reaction mixture affords 4,5-dimethyl-6-oxo-7-bromo-7-propyl-7,8.-dihydro-6H-indeno[5,4-b]furan-2-carboxylic acid which melts at 233°C. after recrystallization from toluene.

Elemental analysis for $C_{17}H_{17}BrO_4$; Calc.: C, 55.90; H, 4.69; Found: C, 56.75; H, 4.91.

Step B:
4,5-Dimethyl-6-oxo-7-propyl-6H-indeno[5,4-b]furan-2-carboxylic acid

A solution of 4,5-dimethyl-6-oxo-7-bromo-7-propyl-7,8-dihydro-6H-indeno[5,4-b]furan-2-carboxylic acid (1.2 g., 0.0033 mole) and 1,5-diazabicyclo [4.3.0]-5-nonene (0.8 ml.) in dimethylsulfoxide (8 ml.) is stirred at 25°C. for one hour then treated with water (30 ml.) hydrochloric acid (5 ml.) and ethanol (20 ml.) affording 4,5-dimethyl-6-oxo-7-propyl-6H-indeno[5,4-b]furan-2-carboxylic acid as a red solid which melts at 242°C. after recrystallization from nitromethane.

Elemental analysis for $C_{17}H_{16}O_4$; Calc.: C, 71.82; H, 5.67; Found: C, 71.31; H, 5.72.

EXAMPLE 11

4,5-Dimethyl-6-oxo-7-propylidene-7,8-dihydro-6H-indeno-[5,4-b]furan-2-carboxylic acid A stirred solution of 4,5-dimethyl-6-oxo-7-bromo-7-propyl-7,8-dihydro-6H-indeno[5,4-b]furan-2-carboxylic acid (0.8 g., 0.0022 mole) and anhydrous lithium bromide (0.49 g., 0.0056 mole) in dimethylformamide (10 ml.) is heated at 95° in an inert atmosphere for one hour then poured into water (100 ml.) affording 4,5-dimethyl-6-oxo-7-propylidene-7,8-dihydro-6H- indeno-[5,4-b]furan-2-carboxylic acid which melts at 301°C after recrystallization from ethanol.

Elemental analysis for $C_{17}H_{16}O_4$; Calc.: C, 71.82; H, 5.67; Found: C, 71.53; H, 5.66.

EXAMPLE 12

4,5-Dimethyl-6-oxo-7-propyl-1,2,7,8-tetrahydro-6H-indeno-[5,4-b]furan-2-carboxylic acid

Step A:
4,5-Dimethyl-6-hydroxy-7-propyl-1,2,7,8-tetrahydro-6H-indeno[5,4-b]-furan-2-carboxylic acid A solution of 4,5-dimethyl-6-oxo-7-propyl-7,8-dihydro-6H-indeno[5,4-b]furan-2-carboxylic acid (2.0 g., 0.007 mole) in aqueous sodium bicarbonate (40 ml.) is treated with 1% sodium amalgam (120 g.) and stirred at 25°C. for 18 hours. The mercury is separated and the aqueous phase is acidified with hydrochloric acid affording 2.0 g. (99%) of 4,5-dimethyl-6-hydroxy-7-propyl-1,2,7,8-tetrahydro-6H-indeno[5,4-b]furan-2-carboxylic acid which melts at 161°C. after recrystallization from nitromethane.

Elemental analysis for $C_{17}H_{22}O_4$: Calc.: C, 70.32; H, 7.64; Found: C, 70.52; H, 7.44.

Step B:
4,5-Dimethyl-6-oxo-7-propyl-1,2,7,8-tetrahydro-6H-indeno[5,4-b]furan-2-carboxylic acid A stirred suspension of 4,5-dimethyl-6-hydroxy-7-propyl-1,2,7,8-tetrahydro-6H-indeno[5,4-b]furan-2-carboxylic acid (5.0 g., 0.017 mole) in acetone (250 ml.) is treated over a ten minute period with an oxidizing reagent prepared from chromium trioxide (2.5 g. and concentrated sulfuric acid (2.2 ml.) in water (18 ml.). The acetone solution is decanted from the precipitated chromium salts and poured into water (700 ml.) affording 4,5-dimethyl-6-oxo-7-propyl-1,2,7,8-tetrahydro-6H-indeno-[5,4-b]furan-2-carboxylic acid which melts at 161°C. after recrystallization from butyl chloride.

Elemental analysis for $C_{17}H_{20}O_4$: Calc.: C, 70.81; H, 6.99; Found: C, 70.33; H, 6.99.

EXAMPLE 13

4,5-Dimethyl-6-oxo-7-propyl-1,2-dihydro-6H-indeno[5,4-b]-furan-2-carboxylic acid

Step A:
4,5-Dimethyl-6-oxo-7-bromo-7-propyl-1,2,7,8-tetrahydro-6H-indeno[5,4-b]-furan-2-carboxylic acid A stirred suspension of 4,5-dimethyl-6-oxo-7-propyl-1,2,7,8-tetrahydro-6H-indeno[5,4-b]furan-2-carboxylic acid (14 g., 0.00486 mole) in acetic acid (15 ml.) is treated with a solution of bromine (0.8 g., 0.005 mole) in acetic acid (5 ml.) during a three minute period. The reaction mixture is poured into water (100 ml.) containing sodium bisulfate (1 g.), extracted with ether, washed with water, dried over magnesium sulfate and the ether distilled at reduced pressure affording an oil which on trituration with cyclohexane affords 4,5-dimethyl-6-oxo-7-bromo-7-propyl-1,2,7,8-tetrahydro-6H-indeno[5,4-b]furan-2-carboxylic acid (1.4 g., 78%) as a white solid which melts at 78°C. and is used in the next step without further purification.

Step B:
4,5-Dimethyl-6-oxo-7-propyl-1,2,dihydro-6H-indeno[5,4-b]furan-2-carboxylic acid A solution of 4,5-dimethyl-6-oxo-7-bromo-7-propyl-1,2,7,8-tetrahydro-6H-indeno[5,4-b]furan-2-carboxylic acid (0.70 g., 0.0019 mole) and 1,5-diazabicyclo-[4.3.0]-5-one (0.5 ml.) in dimethylsulfoxide (5 ml.) is stirred at 25°C. in an inert atomsphere for 1 ½ hours, treated with water (15 ml.) acidified with hydrochloric acid, extracted with ether washed with water and dried over magnesium sulfate. The ether is evaporated at reduced pressure and the crude product crystallized from nitromethane (10 ml.) affording 4,5-dimethyl-6-oxo-7-propyl-1,2-dihydro-6H-indeno[5,4-b]furan-2-carboxylic acid as a red solid which melts at 212°C.

Elemental analysis for $C_{17}H_{18}O_4$: Calc.: C, 71.31; H, 6.34; Found: C, 71.08; H, 6.34.

EXAMPLE 14

4,5-Dimethyl-6-oxo-7-propylidene-1,2,7,8-tetrahydro-6H-indeno[5,4-b]furan-2-carboxylic acid A stirred solution of 4,5-dimethyl-6-oxo-7-bromo-7-propyl-1,2,7,8-tetrahydro-6H-indeno[5,4-b]furan-2-carboxylic acid (0.7 g., 0.0019 mole) and lithium bromide (0.5 g., 0.0057 mole) in dimethylformamide (10 ml.) is heated at 95°C. for one hour in an inert atmosphere then poured into water (50 ml.) affording 4,5-dimethyl-6-oxo-7-propylidene-1,2,7,8-tetrahydro-6H-indeno[5,4-b]-furan-2-carboxylic acid as a cream colored solid which melts at 229°C. after recrystallization from ethanol.

Elemental analysis for $C_{17}H_{18}O_4$: Calc.: C, 71.31; H, 6.34; Found: C, 71.28; H, 6.45.

The compounds of this invention can be administered in a wide variety of therapeutic dosages in conventional vehicles as, for example, by oral administration in the form of a tablet or by intravenous injection. Also, the daily dosage of the products may be varied over a wide range as, for example, in the form of scored tablets containing 5, 10, 25, 100, 150, 250 and 500 mg. of the active ingredient for the symptomatic adjustment of the dosage to the individual being treated.

A suitable unit dosage form of the product of this invention can be administered by mixing 50 mg. of an indenofuran or a suitable salt, ester or amide derivative thereof of the present invention with 149 mg. of lactose and 1 mg. of magnesium sterate and placing the 200 mg. mixture into a No. 1 gelatin capsule. Similarly by employing more of the active ingredient and less lactose, other dosage forms can be put up in No. 1 gelatin capsules and should it be necessary to mix more than 200 mg. of ingredients together larger capsules may be employed. Compressed tablets, pills or other desired unit dosages can be prepared to incorporate the compounds of this invention by conventional methods and if desired can be made up as elixirs or as injectable solutions by methods well known to pharmacists.

It is also within the scope of this invention to combine two or more of the compounds of this invention into a unit dosage form or to combine one or more of the compounds of this invention with other known diuretics and saluretics or with other desired therapeutic and/or nutritive agents in dosage unit form.

The following example is included to illustrate the preparation of representative dosage form:

EXAMPLE 15

Dry-filled capsules containing 50 mg. of active ingredient per capsule.

|  | Per Capsule |
|---|---|
| 4',5'-Dichloro-6'-oxo-1',2',7',8'-tetrahydrospiro (cyclopentane-1,7'-6'-H-indeno[5,4-b]furan)-2'-carboxylic acid | 50 mg. |
| Lactose | 149 mg. |
| Magnesium stearate | 1 mg. |
| Capsule (Size No. 1) | 200 mg. |

Similar dry-filled capsules are prepared by replacing the active ingredient of the above example by the sodium, diethanolamine, and triethanolamine salt thereof, respectively.

It will be apparent from the foregoing description that the indenofurans of this invention constitute a valuable class of compounds which have not been prepared heretofore. One skilled in the art will also appreciate that the processes disclosed in the above examples are merely illustrative and are capable of nonsubstantive modification without departing from the intended scope of the present invention as claimed.

What is claimed is:

1. A compound having the formula:

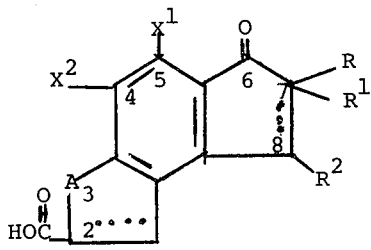

wherein the dotted lines indicate no unsaturation or 1,2-,7,8-, and 1,2,7,8- unsaturated embodiments; A is oxygen or sulfur; R is hydrogen, lower alkyl or halo; $R^1$ is lower alkyl or cycloalkyl having from 3–6 carbon atoms; R and $R^1$, together with the carbon atom to which they are attached, may be joined to form a cycloalkyl radical having from 3 to about 6 carbon atoms; $R^2$ is hydrogen, lower alkyl or phenyl; $X^1$ is lower alkyl or halo; $X^2$ is hydrogen, lower alkyl or halo; a 7-alkylidene embodiment is characterized in that the substituent at the 7-position is $=CR^3R^4$; wherein $R^3$ and $R^4$ are independently selected from a group consisting of hydrogen, lower alkyl, cycloalkyl having from 3 – 6 carbon atoms, and phenyl; and if the dotted line at the 7,8-position represents unsaturation the R radical is nonexistent; and the non-toxic, pharmacologically acceptable salt and lower alkyl ester derivatives thereof.

2. The compound of claim 1 wherein R is hydrogen, lower alkyl having from 1 to 6 carbon atoms, or halogen selected from a group consisting of chloro, bromo and fluoro; $R^1$ is lower alkyl having from 1 to 6 carbon atoms and cycloalkyl having from 3 to 6 carbon atoms; R and $R^1$ are joined together with the carbon atom to which they are attached to form a cycloalkyl radical having from 3 to 6 carbon atoms; $R^2$ is hydrogen, lower alkyl having from 1 to 6 carbon atoms or phenyl; $R^3$ and $R^4$ are independently selected from hydrogen, lower alkyl having from 1 to 6 carbon atoms, cycloalkyl having from 3 to 6 carbon atoms and phenyl; $X^1$ is lower alkyl having from 1 to 6 carbon atoms or halogen selected from a group consisting of chloro, fluoro and bromo; $X^2$ is hydrogen, lower alkyl having from 1 to 6 carbon atoms, or halogen selected from the group consisting of chloro, fluoro and bromo; and the non-toxic pharmaceutically acceptable salt and lower alkyl ester derivatives thereof.

3. The compound of claim 2 wherein A is oxygen.

4. The compound of claim 3 wherein $R^2$ is phenyl or hydrogen; R is hydrogen, methyl, chloro or bromo; $R^1$ is lower alkyl having from 1 to 6 carbon atoms, cycloalkyl having from 5 to 6 carbon atoms; $R^3$ and $R^4$ are independently selected from hydrogen and lower alkyl having from 1 to 6 carbon atoms.

5. The compound of claim 4 which is 4,5-dimethyl-6-oxo-7-isopropyl-1,2,7,8-tetrahydro-6H-indeno-[5,4-b]furan-2-carboxylic acid.

6. The compound of claim 4 which is 4,5-dimethyl-6-oxo-7-isopropyl-7,8-dihydro-6H-indeno-[5,4-b]-furan-2-carboxylic acid.

7. The compound of claim 4 which is 4,5,7-trimethyl-6-oxo-7-isopropyl-1,2,7,8-tetrahydro-6H-indeno-[5,4-b]furan-2-carboxylic acid.

8. The compound of claim 4 which is 4,5-dimethyl-6-oxo-7-isopropyl-6H-indeno[5,4-b]furan-2-carboxylic acid.

9. The compound of claim 4 which is 4,5-dimethyl-6-oxo-7,8-dihydro-7-isopropylidene-6H-indeno-[5,4-b]furan-2-carboxylic acid.

10. The compound of claim 4 which is 4,5-dichloro-7-ethyl-6-oxo-8-phenyl-1,2,7,8-tetrahydro-6H-indeno[5,4-b]furan-2-carboxylic acid.

11. 4',5'-Dichloro-6'-oxo-1',2',7',8'-tetrahydrospiro-(cyclopentane-1,7',-6' H-indeno[5,4-b]furan)-2'-carboxylic acid and its nontoxic pharmaceutically acceptable salt and lower alkyl ester derivatives.

12. 4,5-Dimethyl-6-oxo-7-propyl-7,8-dihydro-6H-indeno[5,4-b]furan-2-carboxylic acid and its nontoxic pharmaceutically acceptable salt and lower alkyl ester derivatives.

13. 4,5-Dimethyl-6-oxo-7-bromo-7-propyl-7,8-dihydro-6H-indeno[5,4-b]furan-2-carboxylic acid and its nontoxic pharmaceutically acceptable salt and lower alkyl ester derivatives.

14. 4,5-Dimethyl-6-oxo-7-propyl-6H-indeno-[5,4-b]furan-2-carboxylic acid and its nontoxic pharmaceutically acceptable salt and lower alkyl ester derivatives.

15. 4,5-Dimethyl-6-oxo-7-propylidene-7,8-dihydro-6H-indeno[5,4-b]furan-2-carboxylic acid and its nontoxic pharmaceutically acceptable salt and lower alkyl ester derivatives.

16. 4,5-Dimethyl-6-hydroxy-7-propyl-1,2,7,8-tetrahydro-6H-indeno[5,4-b]-furan-2-carboxylic acid and its nontoxic pharmaceutically acceptable salt and lower alkyl ester derivatives.

17. 4,5-Dimethyl-6-oxo-7-propyl-1,2,7,8-tetrahydro-6H-indeno[5,4-b]furan-2-carboxylic acid and its nontoxic pharmaceutically acceptable salt and lower alkyl ester derivatives.

18. 4,5-Dimethyl-6-oxo-7-bromo-7-propyl-1,2,7,8-tetrahydro-6H-indeno[5,4-b]furan-2-carboxylic acid and its nontoxic pharmaceutically acceptable salt and lower alkyl ester derivatives.

19. 4,5-Dimethyl-6-oxo-7-propyl-1,2-dihydro-6H-indeno[5,4-b]furan-2-carboxylic acid and its nontoxic pharmaceutically acceptable salt and lower alkyl ester derivatives.

20. 4,5-Dimethyl-6-oxo-7-propylidene-1,2,7,8-tetrahydro-6H-indeno[5,4-b]furan-2-carboxylic acid and its nontoxic pharmaceutically acceptable salt and lower alkyl ester derivatives.

* * * * *